United States Patent [19]

Kumana

[11] 4,350,690
[45] Sep. 21, 1982

[54] STEROID COMPOSITION

[75] Inventor: Cyrus R. Kumana, Ancaster, Canada

[73] Assignee: Cressington Investments Ltd., Hong Kong, Hong Kong

[21] Appl. No.: 200,872

[22] Filed: Oct. 27, 1980

[51] Int. Cl.³ .............................................. A61K 31/56
[52] U.S. Cl. ................................................... 424/243
[58] Field of Search ........................................ 424/243

[56] References Cited

U.S. PATENT DOCUMENTS 4,013,792  3/1977  Eichman ............................ 424/243
4,225,597  9/1980  Finckenor .......................... 424/243

OTHER PUBLICATIONS

"Current Therapy" (1979) Article by Korelitz, pp. 391–397.

*Primary Examiner*—Elbert L. Roberts
*Attorney, Agent, or Firm*—Lawrence Rosen

[57] ABSTRACT

A steroid pharmaceutical composition for administration as an enema to patients for treatment of inflammatory bowel disorders comprises a liquid suspension of total volume from about 50 to about 150 mls, containing an effective amount in the range of about 0.1 mg to about 2 mg of a steroid drug with high topical activity, such as beclomethasone dipropionate. Administration of such enema compositions to the patient, using such appropriately potent but low doses, has been found to be systemically inactive (presumably due to metabolism by the liver), so that adverse side effects otherwise experienced with such treatment can be avoided.

4 Claims, No Drawings

STEROID COMPOSITION

FIELD OF THE INVENTION

This invention relates to medical compositions and administration thereof, more particularly to compositions for treatment of disorders of the bowel of a patient.

BACKGROUND OF THE INVENTION AND PRIOR ART

Ulcerative Colitis is an inflammatory disorder of the large bowel (colon and rectum) of unknown cause. It is usually worse in the rectum and may extend for varying distances along the colon proximally (and may involve the entire colon). There are other types of inflammatory disorders of the large bowel which are sometimes confined to the rectum which may be a very mild form of ulcerative colitis or a slightly different syndrome with very similar pathology. Crohn's Disease is yet another type of inflammatory bowel disease of unknown etiology which also affects the large bowel occasionally. There is no known cause for these conditions and the approach to treatment has been the use of non-specific anti-inflammatory drugs. The most effective treatment is the use of steroid drugs which are potent anti-inflammatory agents, but these also have a wide variety of side effects which include suppression of the hypothalamic pituitary adrenal (HPA) axis. These steroid drugs (e.g. prednisone) are most commonly given orally and occasionally parenterally. They are absorbed and produce their therapeutic effects on the colon as part of their broad anti-inflammatory action but because they enter the system circulation their major side effects are not avoided.

Many steroid drugs have very potent topical activity which has been successfully utilized in the treatment of asthma and certain skin disorders. However, since absorption occurs even through the skin, they also produce the same side effects when applied to the skin, as steroids taken systemically.

It has been a practice hitherto to treat patients with inflammatory bowel disorders such as distal ulcerative colitis, by administering a steroid drug as an enema. Whilst this applies the drug primarily to the location where its topical treatment effects are required, it is well recognized that the drug still enters the systemic circulation and results in side efffects. This occurs with the smallest doses of steroid enemas likely to be effective (e.g. 5 mg. betamethasone or 100 mg. hydrocortisone enema every night).

SUMMARY OF THE INVENTION

The present invention is based on the discovery that certain steroid drugs, notably beclomethasone dipropionate, can be administered to a patient as an enema, in a dosage which is effective for topical treatment of the bowel (e.g. in the treatment of distal ulcerative colitis), but without significant entry of the drug into the systemic circulation to cause the usual side effects. It appears that an effective dose of the selected steroid drug can be introduced into the gut as an enema and that the whole dose appears to be effectively metabolized and inactivated (possibly by the liver) before reaching the systemic circulation. The side effects are therefore very substantially reduced. Venous blood draining from the small and large bowel eventually passes into the liver through the portal vein. So long as the dose of the selected steroid drug used in the enema is not excessive, the liver appears to be capable of inactivating all the drug it receives, before any can reach the systemic circulation.

Thus according to the present invention, there is provided an enema composition for nightly administration as topical treatment for a patient having inflammatory bowel disorder, said enema composition having a total volume of from about 50 to about 150 mls and comprising, as active ingredient, an effective amount in the range from about 0.1 mg to about 2 mg of a highly topically active steroid drug, and a process of treatment of subjects by rectal administration of such composition.

DESCRIPTION OF THE PREFERRED EMBODIMENTS

The enema composition according to the present invention has been primarily developed for use in the treatment of distal ulcerative colitis, for which it is commonly administered to a patient rectally every night (or less often) immediately prior to the patient's retiring. However, the compositions also show utility in treatment of other inflammatory bowel disorders (including isolated proctocolitis and large bowel Crohn's disease) in which steroid treatment has an effect. By means of the invention, topical steroid treatment is used with good effect to obtain its beneficial local actions whilst avoiding systemic side effects and HPA suppression.

The preferred drugs for use in the composition of the present invention are beclomethasone dipropionate and betamethasone-17-valerate, on account of their high topical activity and effectiveness at low dosages. However, the invention is not restricted thereto, and relates to any steroid drug which is topically active for effective treatment of inflammatory diseases of the large bowel, at the dosage level of not more than about 2 mg, preferably not more than about 1 mg, administered at a time, e.g. daily. Such drugs, given in such dosage through the gastro-intestinal tract, should not enter the systemic circulation, and hence systemic adverse effects resulting from their presence in the systemic circulation are avoided. The most preferred drug is beclomethasone dipropionate, on account of its very high topical anti-inflammatory activity. This drug can therefore be used effectively in very small doses, in the enema compositions of the invention, and will not enter the systemic circulation to any significant extent. Other steroid drugs (such as betamethasone-17-valerate) may also be useful, provided that they are effective in treating the patient's bowel disorder in such small doses, and that all the dose absorbed by the gut is inactivated before reaching the systemic circulation.

The enema dose units are prepared in suitable sizes, normally 50–150 ml and (preferably about 100 mls of liquid), for daily administration in accordance with known practice. Normally they comprise suspensions of the selected drug in a suitable liquid vehicle. Since the drug is essentially insoluble in water, it is necessary to include in any aqueous liquid formulation of the drug suitable acceptable suspending agents, for example cellulose compounds such as methyl cellulose, carboxymethyl cellulose, sugars, starches and the like, and/or surfactants or soaps, e.g. Tween 20 or Tween 80, so as to form a suitably stable suspension with appropriate viscosity characteristics. The composition is arranged so that the solid drug particles remain suspended or, if perchance they settle out, can be readily re-dispersed and suspended on shaking. The enema composition may also contain stabilizers, for example sodium metabisulfite, EDTA salts, antioxidants such as ascorbates, etc., and preservatives to guard against microbial attack, e.g. various benzoates, with broad antibacterial activity spectrum, phenyl mercuric nitrate, benzyl alcohol, chlorhexadine, sorbic acid, etc., or even broad spectrum antibiotics, to ensure shelf life. The enema composition may be prepared and stored in bulk and broken down to the required amounts immediately prior to administration. Ethyl alcohol may also be used, to aid in the initial powder dispersion in the aqueous medium, and also to act as a preservative. If desired, the drug particles can be passed through a micronizer to prepare ultrafine particles thereof for ease of dispersion. Apart from the specific steroid drug, the enema composition and its preparation and method of administration are essentially conventional, and contain the ingredients known to be useful in similar formulations, and well known to those skilled in this field.

The invention and its application are illustrated in the following specific examples.

PREPARATION OF ENEMA COMPOSITIONS

Apparoximately 30 mg of beclomethasone dipropionate (BDP), obtained from a proprietary inhaler, were dried in a desiccator overnight. The powder so formed was dissolved in 16 mls of 95% ethanol. The final enema was made up by mixing 7.5 mls of this solution with methylhydroxybenzoate 375 mg and propylhydroxybenzoate 192 mg, sodium ethylenediamine tetraacetate 150 mg, sodium metabisulphite 750 mg, methyl cellulose BDH product #29217 7.5 g, and distilled water to make up a final volume of 1500 mls. The suspension so formed was well mixed by shaking and packaged as 100 ml doses (expected to contain 1 mg. of BDP) in Wheaton enema bottles. Using a quantitative thin layer chromatography assay (developed locally), freshly made enema suspension was found to contain half the expected concentration (0.5 mg/100 ml) of intact betamethasone dipropionate and an identical concentration was detected after 6 weeks storage at room temperature.

EXAMPLE 1

Six healthy volunteers (aged 24–40) (4 males) took part in a double blind randomized crossover study with betamethasone (Betnesol) and BDP enemas. For about 36 hours prior to taking an enema, each subject remained on a liquid diet and took regular mild laxatives to ensure an empty rectum. Either a betamethasone enema or a BDP enema was introduced on retiring to sleep and retained overnight. The following morning (between 8 a.m. and 9 a.m.) venous blood samples were drawn and collected in heparinised tubes—for determination of plasma cortisol concentration. After at least one week, each subject repeated the procedure with the alternative enema. A morning venous blood sample was also drawn from each subject when no enema had been taken overnight to determine a control morning plasma cortisol concentration.

All the blood samples were freshly separated and the plasma stored at $-20°$ for later analysis. In batches, samples were thawed and well shaken and the plasma cortisol concentration determined in duplicate using a standard radioimmunossay.

The results obtained are shown in Table 1. In every subject, only the morning plasma cortisol concentration obtained after a single overnight betamethasone enema was markedly suppressed. Using paired t tests, there was a significant difference ($P<0.02$) between the morning plasma cortisol concentrations post betamethasone enema and the morning plasma cortisol concentrations post BDP enema, and similarly there was a significant difference ($P<0.01$) between the morning plasma cortisol concentration post betamethasone enema and the control morning cortisol concentrations. There was no significant difference ($P>0.1$) between the control morning cortisol concentrations and the morning cortisol concentrations post BDP enema.

TABLE I

MORNING (8–9 A.M.) PLASMA CORTISOL CONCENTRATION ($\mu g/dl$)

| Subject | Control | Post Overnight betamethasone (5 mg) enemas | Post Overnight BDP (1 mg) enemas |
|---|---|---|---|
| 1 | 22.1 | 1.8 | 17.2 |
| 2 | 29.1 | 1.9 | 50.3* |
| 3 | 18.7 | 1.7 | 17.0 |
| 4 | 13.4 | 1.5 | 17.3 |
| 5 | 21.2 | 1.5 | 19.2 |
| 6 | 13.5 | 0.1 | 16.2 |
| Mean ± SD | 19.7 ± 5.9 | 1.4 ± 0.7 | 22.9 ± 13.5 |

*This anomalous high value may be explained by the subject's anxiety before blood was withdrawn; laboratory error is unlikely as the sample was rechecked in duplicate.

In each of the 6 healthy volunteers the conventional (betamethasone phosphate 5 mg) enema taken at night markedly suppressed the morning plasma cortisol concentration (Table I), in a fashion exactly analogous to the normal response following an oral overnight dexamethasone test. In contrast, after the overnight use of a 1 mg BDP enema, there was no adreno-cortical suppression, which suggests that no active steroid reached the systemic circulation. Assay of the final enema suspension confirmed that it contained intact BDP (though at half the predicted concentration). Thus the dose of active steroid delivered with the BDP enema was appropriate (i.e. its beneficial local activity was at least comparable to, if not greater than, that delivered with a betamethasone enema). As the enema's BDP concentration remained unchanged after 6 weeks storage at room temperature, it is apparent that once in the enema the active principle (BDP) remains stable and that the enema remains therapeutic.

EXAMPLE 2

Case Study and Report

A 36-year old man had suffered from ulcerative proctitis for about five years. Initially his diarrhoea and rectal bleeding were reasonably controlled with daily sulphasalazine and short course of hydrocortizone suppositories during exacerbations. Two years later the disease had progressed up to the sigmoid colon as judged by barium enema examination. He was then treated with nightly 5 mg. betamethasone enemas for periods of up to a month. The diarrhoea, bleeding and sigmoidoscopic appearance improved while taking the enemas; however, there was invariable recurrence on discontinuing them. To help control his symptoms oral prednisone was added to his treatment for a period of one year. Despite sulphasalazine combined with oral and rectal steroids, the disease activity was not completely controlled and the patient went on to develop gross cushinoid features. The prednisone was gradually tapered off, but nightly betamethasone enemas were needed to control symptoms. Three years after onset, the disease had progressed up to mid descending colon.

During the next 12 months, the patient continued to require one betamethasone enema at least every third night; and during exacerbations enemas were taken nightly. Serial sigmoidoscopic examinations showed various grades of inflammation. He became moon faced, had a voracious appetite and gained weight, lost his sexual drive, and his morning plasma cortisol concentration was <0.5 µg/dl; and following 0.25 mg I.M. adrenocorticoptropic hormone (Cortrosyn) the plasma cortisol concentrations were <0.5 µg/dl at 30 minutes and 1.1 µg/dl at 60 minutes, indicating severe HPA suppression.

The betamethasone enemas were discontinued, and BDP enemas in accordance with this invention and as described in Example 1 were administered, one every night for two weeks. Transiently the patient developed muscular aches and pains, and backache and a dry skin. These features are all symptoms of systemic steroid withdrawal, thus tending to confirm that, unlike his previous steroid (betamethasone) enema, steroid from his present enema did not reach the systemic circulation. At the end of the two week course there was no diarrhoea, he had two bowel movements daily with soft formed stool. Sigmoidoscopy revealed an almost normal mucosa, with only minimal erythema. Despite stopping the steroid enemas, he remained asymptomatic for one month and then had recurrence of diarrhoea (but no blood), at which time sigmoidoscopy revealed mild to moderate inflammation. BDP enemas were recommenced nightly and his colitic symptoms were controlled to the same extent as before.

The patient continued to be maintained on regular BDP enemas with reasonable control of symptoms, but whenever the enemas were discontinued there was a prompt exacerbation. The patient no longer had a cushinoid habitus, lost his voracious appetite, regained his sexual drive, and his morning plasma cortisol concentration was measured at 3.7 µg/dl.

I claim:

1. The process of alleviating topical disorders of the rectum and distal colon of a patient, which comprises rectally administering to said patient a liquid aqueous suspension containing as active ingredient from about 0.1 mg to about 2 mg of a steroid drug of high topical activity and selected from the group consisting of beclomethasone dipropionate and betamethasone-17-valerate, the total volume of said suspension being from about 50 to about 150 mls.

2. The process of claim 1 wherein said suspension contains from about 0.1 mg to about 1 mg of steroid drug.

3. The process of claim 2 wherein the steroid drug is beclomethasone dipropionate.

4. The process of claim 2 wherein the steroid drug is betamethasone-17-valerate.

* * * * *